US012653653B2

(12) United States Patent
Kato

(10) Patent No.: US 12,653,653 B2
(45) Date of Patent: Jun. 16, 2026

(54) METHOD OF PRODUCING BLOCK FOR DENTAL PROSTHESES, AND METHOD OF PRODUCING DENTAL PROSTHESIS

(71) Applicant: GC CORPORATION, Sunto-gun (JP)

(72) Inventor: Katsuhito Kato, Tokyo (JP)

(73) Assignee: GC CORPORATION, Shizuoka (JP)

( * ) Notice: Subject to any disclaimer, the term of this patent is extended or adjusted under 35 U.S.C. 154(b) by 1058 days.

(21) Appl. No.: 17/442,756

(22) PCT Filed: Dec. 20, 2019

(86) PCT No.: PCT/JP2019/050162
§ 371 (c)(1),
(2) Date: Sep. 24, 2021

(87) PCT Pub. No.: WO2020/202666
PCT Pub. Date: Oct. 8, 2020

(65) Prior Publication Data
US 2022/0183803 A1 Jun. 16, 2022

(30) Foreign Application Priority Data

Mar. 29, 2019 (JP) ................................. 2019-069330

(51) Int. Cl.
| | |
|---|---|
| *A61C 13/00* | (2006.01) |
| *A61K 6/833* | (2020.01) |
| *C03C 3/076* | (2006.01) |
| *C03C 4/00* | (2006.01) |
| *C04B 35/01* | (2006.01) |

(52) U.S. Cl.
CPC .......... *A61C 13/0022* (2013.01); *A61K 6/833* (2020.01); *C03C 3/076* (2013.01); *C03C 4/0021* (2013.01); *C04B 35/01* (2013.01)

(58) Field of Classification Search
CPC . A61C 13/0022; A61C 13/0006; A61C 13/08; A61K 6/833; C03C 10/0027;
(Continued)

(56) References Cited

U.S. PATENT DOCUMENTS

2002/0010063 A1 * 1/2002 Schweiger ............. A61K 6/818
106/35
2014/0228196 A1 8/2014 Ritzberger et al.
(Continued)

FOREIGN PATENT DOCUMENTS

CA 2252660 A1 5/1999
EP 3 135 269 A1 3/2017
(Continued)

OTHER PUBLICATIONS

International Search Report for PCT/JP2019/050162 dated Mar. 10, 2020 [PCT/ISA/210].

*Primary Examiner* — Shuangyi Abu Ali
(74) *Attorney, Agent, or Firm* — Sughrue Mion, PLLC

(57) ABSTRACT

Included is a step of exposing a glass blank at a temperature lower than the temperature at which crystals of lithium metasilicate are generated, to an atmosphere at a temperature equal to or higher than the temperature at which crystals of lithium disilicate are generated and lower than the melting point of the crystals of lithium disilicate, to heat the glass blank so that the main crystalline phase of the glass blank is of lithium disilicate.

7 Claims, 4 Drawing Sheets

(58) Field of Classification Search
CPC ..... C03C 2205/06; C03C 3/076; C03C 3/083;
C03C 3/097; C03C 4/0021; C03C 10/00;
C04B 2235/3203; C04B 2235/3217;
C04B 35/01; C04B 35/16; C04B 35/653;
C03B 32/02
See application file for complete search history.

(56) References Cited

U.S. PATENT DOCUMENTS

| | | | |
|---|---|---|---|
| 2016/0287361 | A1 | 10/2016 | Hoshino et al. |
| 2017/0057865 | A1 | 3/2017 | Kim et al. |
| 2017/0281473 | A1 | 10/2017 | Takeuchi et al. |
| 2018/0133113 | A1 | 5/2018 | Hoshino et al. |
| 2018/0244564 | A1 | 8/2018 | Ritzberger et al. |

FOREIGN PATENT DOCUMENTS

| | | | |
|---|---|---|---|
| EP | 3 305 240 | A1 | 4/2018 |
| JP | 2017-193534 | A | 10/2017 |
| JP | 2017-531607 | A | 10/2017 |
| JP | 2018-145084 | A | 9/2018 |
| JP | 2018-526317 | A | 9/2018 |
| WO | 2013/053864 | A2 | 4/2013 |
| WO | 2016/031399 | A1 | 3/2016 |
| WO | 2016/190012 | A1 | 12/2016 |
| WO | 2018/073274 | A1 | 4/2018 |

* cited by examiner

METHOD OF PRODUCING BLOCK FOR DENTAL PROSTHESES, AND METHOD OF PRODUCING DENTAL PROSTHESIS

CROSS REFERENCE TO RELATED APPLICATIONS

This application is a National Stage of International Application No. PCT/JP2019/050162 filed Dec. 20, 2019, claiming priority based on Japanese Patent Application No. 2019-069330 filed Mar. 29, 2019.

TECHNICAL FIELD

The present disclosure relates to a method of producing a block for dental prostheses, and a method of producing a dental prosthesis.

BACKGROUND ART

According to recent technological developments in CAD/CAM (Computer-aided design/Computer-aided manufacturing), in making a dental prosthesis, a designed shape of a dental prosthesis is converted into a given data format to be treated as digital data, and the data is transmitted to a processing machine; thereby, in the processing machine, machining such as cutting and grinding is automatically carried out on the basis of the data, to make a dental prosthesis. This makes it possible to rapidly provide dental prostheses.

It is demanded that such dental prostheses have strength, hardness, chemical durability in the oral environment, and the aesthetics (coloring, texture) same as natural teeth all of which are the basic functions as dental prostheses.

In addition to this, it is also important to machine complex shapes of rough surfaces dental prostheses have in a short time without any faults such as chipping. A material that can be processed in such a short time makes it possible to further rapidly make dental prostheses.

PTL 1 discloses the material for a dental prosthesis which includes given components, to thereby achieve the improvement of the foregoing basic functions and cutting ability.

CITATION LIST

Patent Literature

PTL 1 WO2016/031399

SUMMARY OF INVENTION

Technical Problem

An object of the present disclosure is to provide a method of producing a block for dental prostheses with good machinability.

Solution to Problem

One aspect of the present disclosure is a method of producing a block for dental prostheses before machining to form a dental prosthesis, the method comprising: exposing a glass blank at a temperature lower than the temperature at which crystals of lithium metasilicate are generated, to an atmosphere at a temperature equal to or higher than the temperature at which crystals of lithium disilicate are generated and lower than the melting point of the crystals of lithium disilicate, to heat the glass blank so that the main crystalline phase of the glass blank is of lithium disilicate.

Slow cooling may be included after said exposing to heat the glass blank.

In said exposing to heat the glass blank, the temperature of the atmosphere may be 750° C. to 900° C.

Said exposing the glass blank to the atmosphere may be putting the glass blank in a heating apparatus.

The block may comprise: 60 mass % to 80 mass % of $SiO_2$; 10 mass % to 20 mass % of $Li_2O$; and 3 mass % to 15 mass % of $Al_2O_3$.

Another aspect of the present disclosure is a method of producing a dental prosthesis, the method comprising: producing a block for dental prostheses by the above described producing method, to machine the block. This machining may be cutting.

Advantageous Effects of Invention

According to the present disclosure, a block for dental prostheses with good machinability is obtained.

BRIEF DESCRIPTION OF DRAWINGS

FIG. 3 is an explanatory view of a method of measuring proportion.

DESCRIPTION OF EMBODIMENTS

Examples of specific embodiments will be hereinafter described. The present invention is not limited to these embodiments.

First, a block for dental prostheses which is made by a method of producing a block for dental prostheses according to one embodiment will be described. This block for dental prostheses (hereinafter may be referred to as "block") is in the form of a rectangular column, a round column, or a board (disk). The shape of the block is changed to form a dental prosthesis or a dental prosthesis is cut out from the block, by machining such as cutting and grinding. Among them, a dental prosthesis in the form of a rectangular column or a board (disk) can be made by cutting. Blocks in the form of a rectangular column may be mainly used for cutting out a single dental prosthesis. Blocks in the form of a board may be used for cutting out a plurality of dental prostheses from one block.

Figure 1:
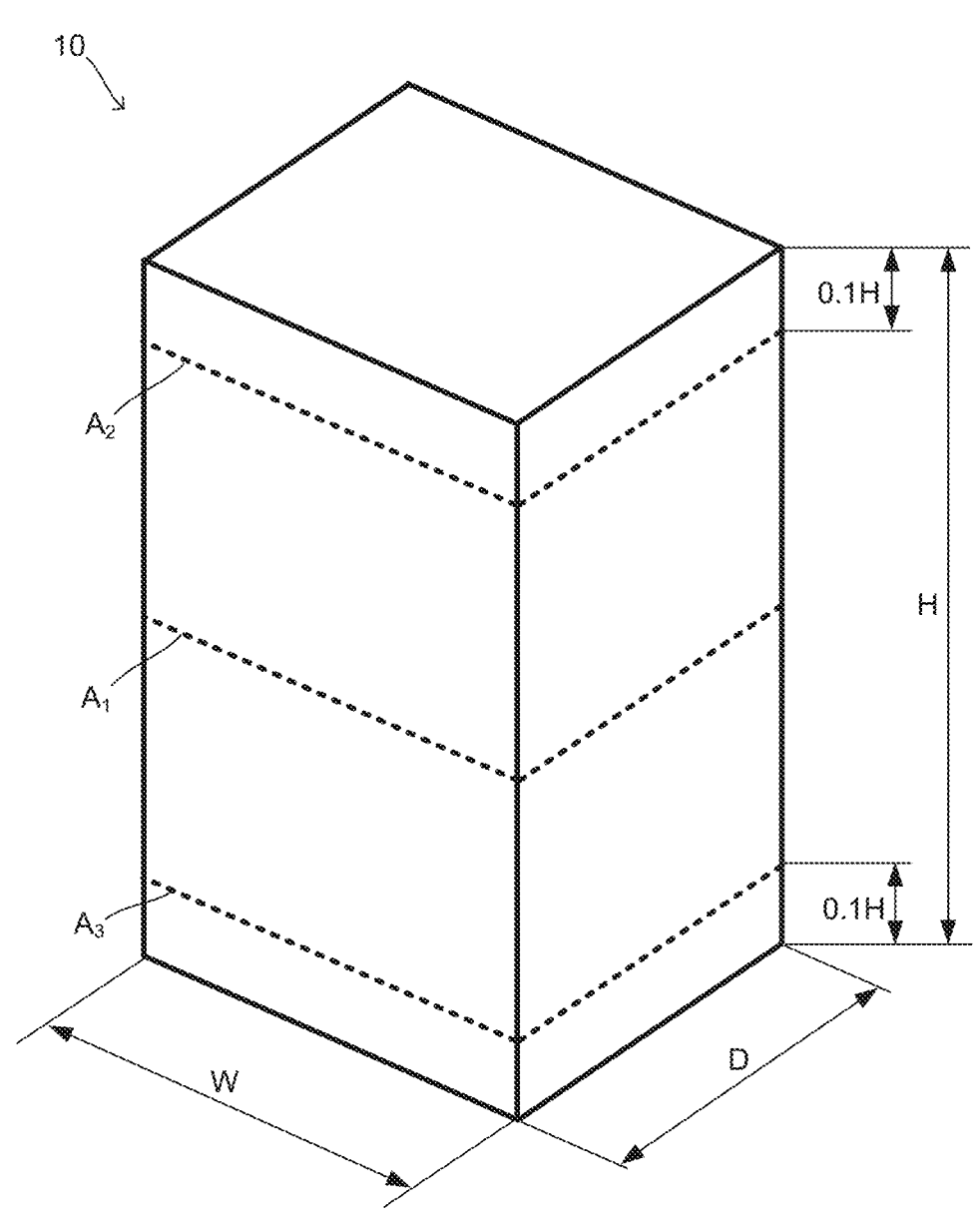
FIG. 1 is an external perspective view of a block for dental prostheses 10.

FIG. 1 is an external perspective view of a block 10 of a rectangular column. The rectangular column may have the width W, the depth D, and the height H within the range of 10 mm to 35 mm each. In contrast, in the case of a block in the form of a board, the block may be formed to have the thickness within the range of 10 mm to 35 mm.

This leads to the block of which a dental prosthesis is easy to be made by cutting.

For making the block according to the present embodiment, its material may be constituted of the following components:

60 mass % to 80 mass % of $SiO_2$;
10 mass % to 20 mass % of $Li_2O$; and
3 mass % to 15 mass % of $Al_2O_3$.
Each of the foregoing components are as follows.

When the block contains less than 60 mass % or more than 80 mass % of $SiO_2$, it is difficult to obtain a homogeneous block. More preferably, 65 mass % to 75 mass % of $SiO_2$ is contained.

When the block contains less than 10 mass % or more than 20 mass % of $Li_2O$, it is difficult to obtain a homogeneous block, and machinability tends to deteriorate. More preferably, 12 mass % to 18 mass % of $Li_2O$ is contained.

When the block contains less than 3 mass % of $Al_2O_3$ on the one hand, machinability tends to deteriorate while lithium disilicate precipitates to constitute a main crystalline phase. When the block contains more than 15 mass % of $Al_2O_3$ on the other hand, the main crystalline phase is not of lithium disilicate, which leads to a tendency to lower strength. More preferably, 3 mass % to 7 mass % of $Al_2O_3$ is contained.

Further, the block for dental prostheses may contain the following components in addition to the foregoing components. The components listed here are not necessarily contained as can be seen from the fact that the amounts thereof may be 0 mass %. It means that at least any one of them may be contained.

The block may contain 0 mass % to 15 mass % of a component for adjusting the melting temperature. This makes it possible to have a suitable melting temperature in production described later. The block may contain more than 15 mass % of some respective components. The improvement of the effect thereof however has its limits. Specific examples of materials for the component for adjusting the melting temperature (melting temperature adjusting materials) include oxides of Na, K, Ca, Sr, Ba, Mg, Rb, Cs, Fr, Be and Ra, which are further preferably as follows:

$Na_2O$: at most 2.8 mass %;
$K_2O$: at most 10 mass %;
CaO: at most 3 mass %;
SrO: at most 10 mass %;
BaO: at most 10 mass %;
MgO: at most 3 mass %;
$Rb_2O$: at most 2.8 mass %;
$Cs_2O$: at most 2.8 mass %;
$Fr_2O$: at most 2.8 mass %;
BeO: at most 3 mass %; and
RaO: at most 10 mass %.

The block may also contain 0 mass % to 10 mass % of a component for forming crystal nuclei. This leads to efficient generation of nuclei to form crystals of lithium disilicate. The upper limit is 10 mass % because the improvement of the effect thereof has its limits even if the block contains more than 10 mass % of such a compound. Here, examples of compounds to function as materials for the component for forming crystal nuclei (crystal nuclei forming materials) include oxides of Zr, P and Ti($ZrO_2$, $P_2O_5$ and $TiO_2$). At this time, the block preferably contains 0 mass % to 10 mass % of at least one selected from $ZrO_2$, $P_2O_5$ and $TiO_2$ in total.

The materials for the block may further include a known coloring material in view of improving aesthetics. Examples thereof include at least one selected from $V_2O_5$, $CeO_2$, $Er_2O_3$, MnO, $Fe_2O_3$ and $Tb_4O_7$.

Next, an embodiment of a method of making a dental prosthesis will be described. This encompasses the embodiment of the method of making the block for dental prostheses. The making method of the present embodiment includes a melting step, a step of making a glass blank, a step of heat treatment, and a processing step.

In the melting step, each of the above described components is molten at a temperature from 1100° C. to 1600° C. This makes it possible to obtain molten glass for the block for dental prostheses. This melting is preferably carried out for several hours in order to obtain sufficient homogeneity.

The step of making a glass blank is a step of obtaining a glass blank having a shape similar to the block for dental prostheses. The molten glass obtained in the melting step is poured into a mold and cooled to a temperature lower than the temperature at which crystals of lithium metasilicate are generated, preferably at most 400° C., more preferably at most 100° C., and further preferably room temperature, to obtain the glass blank. The cooling is carried out in a slow temperature change in order to prevent change in quality of, and cracks in materials.

The step of heat treatment is a step of heating the glass blank obtained in the step of making a glass blank to a temperature equal to or higher than the temperature at which crystals of lithium disilicate are generated and lower than the melting point of the crystals, and more preferably to a temperature within a range of 750° C. to 900° C.

Since rapid heating is preferable in this step, the glass blank, which is cooled in the step of making a glass blank to a temperature lower than the temperature at which crystals of lithium metasilicate are generated, preferably at most 400° C., more preferably at most 100° C., and further preferably room temperature, is heated by, for example, putting the glass blank in a heating apparatus such as a furnace for exposing the glass blank to an atmosphere at a temperature equal to or higher than the temperature at which crystals of lithium disilicate are generated and lower than the melting point of the crystals, and more preferably at a temperature within a range of 750° C. to 900° C. The heating is carried out until the main crystalline phase in the glass blank is of lithium disilicate. Thus, the heating time is not limited, but may be at least 20 minutes. The upper limit of this time is not particularly limited, and may be at most 6 hours.

The heating temperature lower than the temperature at which crystals of lithium disilicate are generated may lead to failure to obtain a lithium disilicate blank whose main crystalline phase is of lithium disilicate. In contrast, the heating temperature equal to or higher than the melting point of crystals of lithium disilicate may lead to softening.

After the rapid heating, heating is stopped, and cooling to room temperature is carried out, which leads to obtainment of the block for dental prostheses whose main crystalline phase is of lithium disilicate. This cooling is carried out in the furnace, and preferably is slow cooling in a slow temperature change in natural cooling in the furnace.

Here, "main crystalline phase" means a crystalline phase, the precipitation rate of crystals of which is the highest in crystalline phases observed on analysis by an X-ray diffractometer.

In the step of heat treatment, rapid heating to a temperature within a predetermined range is necessary as described above. The temperature is not necessarily kept fixed as long as being within a predetermined range, and may change.

The processing step is a step of machining the obtained block for dental prostheses, to process the block to have a shape of a dental prosthesis. The machining method is not particularly limited, and examples thereof include cutting and grinding. This makes it possible to obtain a dental prosthesis.

This processing can be carried out under good conditions for productivity. That is, conventional blocks for dental prostheses whose main crystalline phase is of lithium disilicate are difficult to be efficiently cut because of their poor machinability. Therefore, a block easy to process whose main crystalline phase is not of lithium disilicate (such as a block whose main crystalline phase is of lithium metasilicate) is prepared to be machined, and a step of improving the strength has to follow after the machining, that is, further heat-treating the block to change the main crystalline phase thereof into of lithium disilicate.

In contrast, according to the present embodiment, even a block whose main crystalline phase is of lithium disilicate can be cut and/or ground under the same or better conditions as or than those for processing on a block easy to process whose main crystalline phase is of lithium metasilicate. Heat treatment after processing is not necessary either, which can lead to a dental prosthesis without change in shape as the accuracy of machining is kept.

Figure 2:
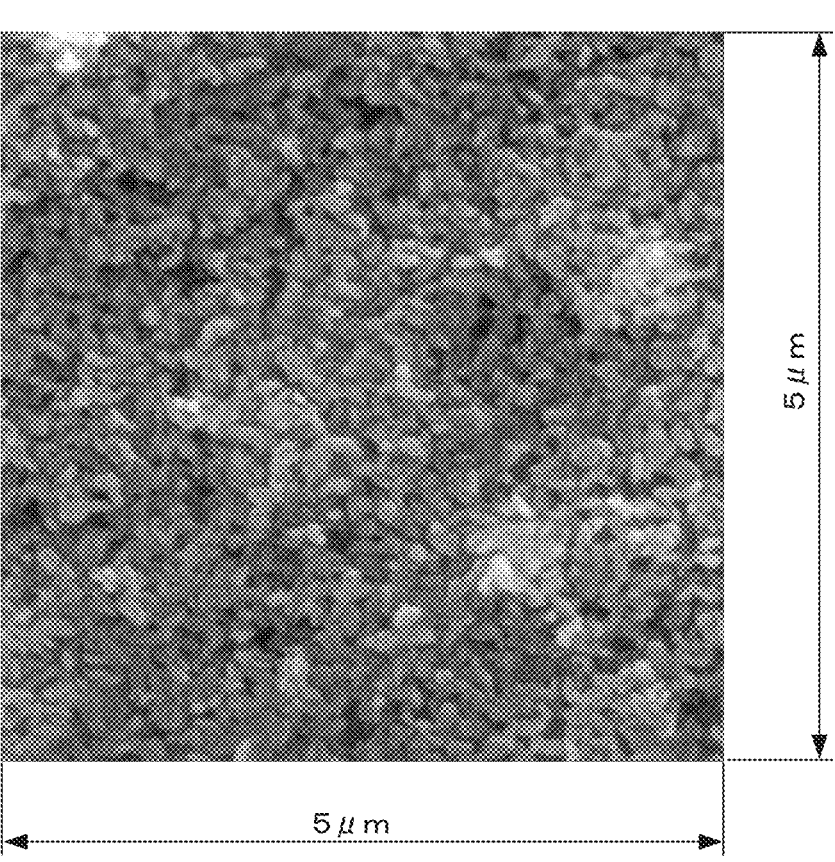
FIG. 2 shows a partially enlarged cross section such that crystals can be seen.

The block made by the producing method of the present embodiment has the following structure. FIG. 2 shows a partially enlarged cross section of the block 10 which is taken along the broken line shown by the reference sign A1 in FIG. 1. This drawing is an enlarged view of a field of view of a length (width direction) of 5 μm and a breadth (depth direction) of 5 μm. Such a drawing may be obtained from a scanning electron microscope (SEM) image.

The main crystalline phase of the block 10 is of lithium disilicate as described above.

The proportion of the total area of crystals having a length of at least 0.5 μm in the crystals of the block 10 appearing within the field of view shown in FIG. 2, to the area of the field of view shown in FIG. 2 (5 μm×5 μm) is preferably, but is not necessarily, at most 21%. The producing method of the present embodiment has only to make it possible to lower this proportion compared to conventional making methods. This proportion is preferably at most 10%, and further preferably at most 1%.

The crystals to be extracted from the appearing crystals, which have a length of at least 0.5 μm, may be limited to crystals of lithium disilicate only.

This makes it possible to cut and/or grind the block whose main crystalline phase is of lithium disilicate under the same or better conditions as or than those for processing conventional blocks that are easy to process (such as a block whose main crystalline phase is of lithium metasilicate). This does not require heat treatment after processing which is, for example, necessary for a block whose main crystalline phase is of lithium metasilicate, which can lead to a dental prosthesis without change in shape as the accuracy of machining is kept.

The proportion as described above is obtained as follows.

Figure 3:
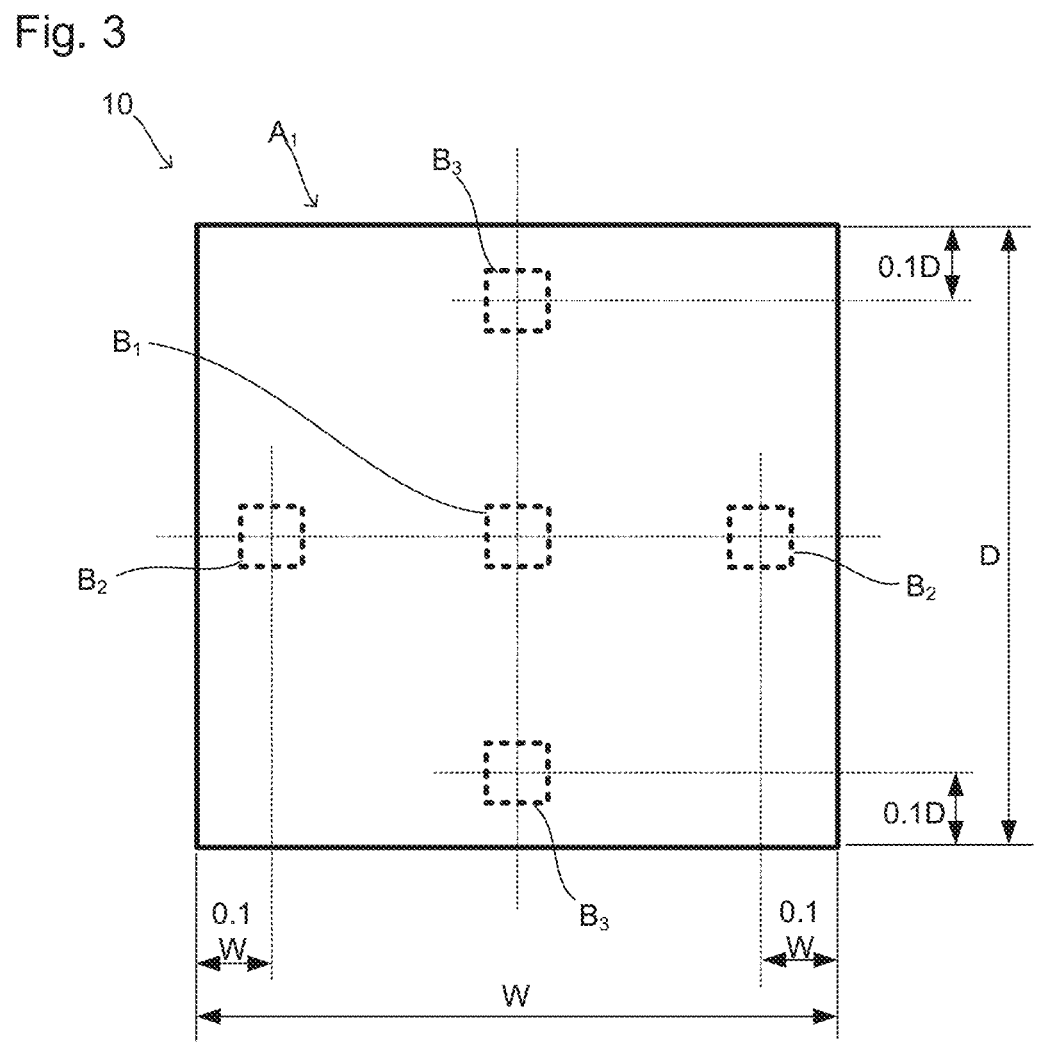

The block 10 shown in FIG. 1 is an example here. Three cross sections that are along the center $A_1$, and along the two edge portions $A_2$ and $A_3$ that are along the places 10% from the end faces to the full length H, in the direction of the largest amount (the height direction in the example in FIG. 1) are obtained. FIG. 3 shows the cross section along the center $A_1$ among the three cross sections.

An image by a scanning electron microscope having the field of view of 5 μm×5 μm as shown in FIG. 2 is obtained for each of the center $B_1$, two end portions $B_2$ that are adjacent to each other across the center $B_1$ in the width direction W at the positions 10% from the end portions to the total width W, and two end portions $B_3$ that are adjacent to each other across the center $B_1$ in the depth direction D at the positions 10% from the end portions to the total depth D; $B_1$ to $B_3$ are shown by the broken lines. This is applied to the cross sections along the center $A_1$, the end portion $A_2$, and the end portion $A_3$. Therefore, five for each cross section, that is, fifteen of such images in total are obtained. The upper part of FIG. 4 shows an example of the obtained images.

Figure 4:
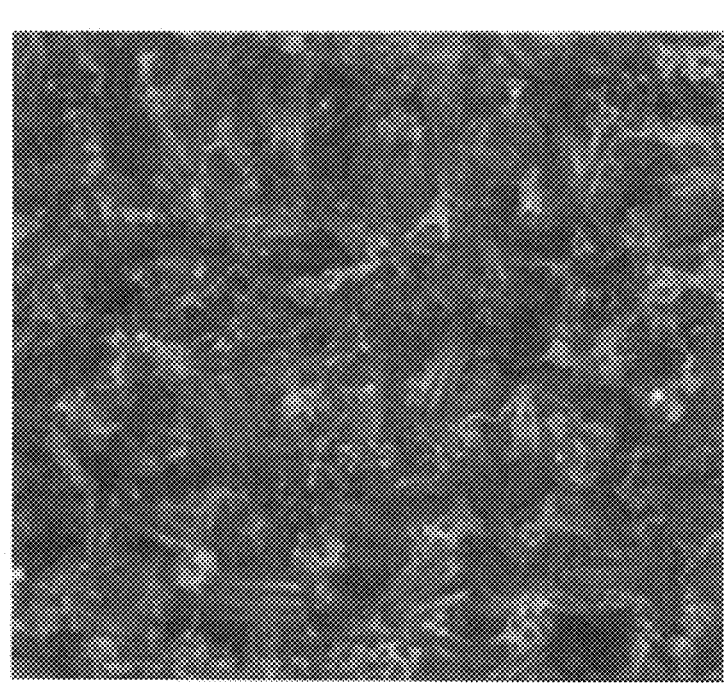
FIG. 4 is another explanatory view of the method of measuring proportion.
Figure 4:
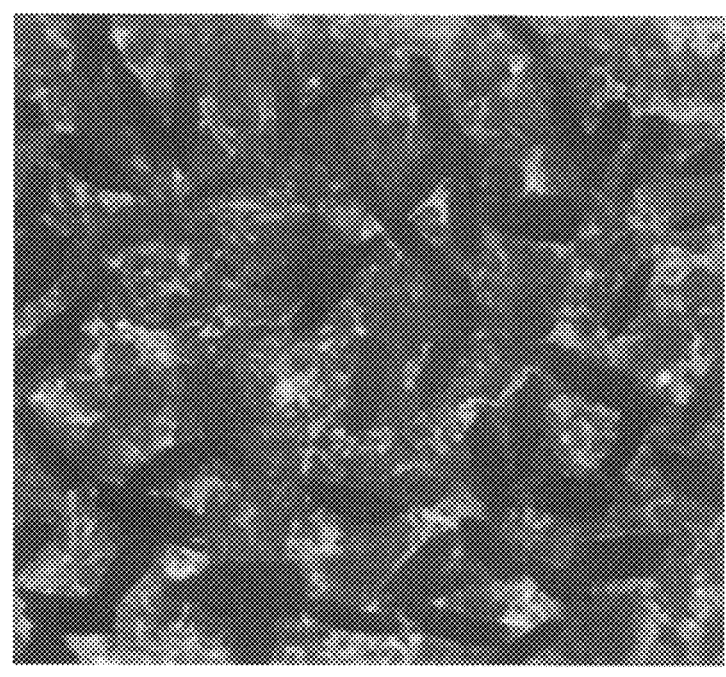

Next, as shown in the lower part of FIG. 4, crystals having a length of at least 0.5 μm (painted parts in the lower part of FIG. 4) are extracted from the crystals appearing in the lower part of FIG. 4, to obtain the total area S of the extracted crystals for each image. Next, the total area S is divided by the area $S_0$ of the field of view of the image (5 μm×5 μm) to be represented in percentages, to obtain the proportion for each individual image. Thus, the respective proportions for the fifteen images are obtained.

The mean value of these respective proportions is calculated to be defined as the proportion.

Here, preferably, no void is seen in the block for dental prostheses. Since the influence of a few voids is believed to be slight, the area of voids to that of the observation range of 60 μm in length (width direction)×60 μm in breadth (depth direction) is preferably at most 2% on average, for each of the fifteen parts where the foregoing proportions are measured.

Preferably, no particulate matter in the coloring material is visually seen in a micrograph at magnification×200 for each of the fifteen parts where the foregoing proportions are measured.

These void and particulate matter may generate the interface with a base material to influence machinability. The presence of any particulate matter in the coloring material may cause color irregularities in dental prostheses.

Such a block for dental prostheses can be surely realized by melting to mold the materials as described above, but not by powder molding.

The foregoing block for dental prostheses, and the dental prosthesis made by processing the block can have strength, hardness, chemical durability in the oral environment, and the aesthetics (coloring, texture) same as natural teeth all of which are the basic functions as dental prostheses. In addition to this, machinability is improved, which makes it possible to carry out machining without any faults under the same or better processing conditions as or than those for conventional blocks for dental prostheses from ceramic for cutting although strength such that heat treatment after processing is not necessary is obtained.

EXAMPLES

In each of Examples 1 to 7 and Comparative Examples 1 to 6, a block was prepared according to the making method by the above described melt molding, to make a dental prosthesis by cutting, and machinability then was evaluated. In each example, the contained components and heat-treating temperature were changed.

The block was a rectangular parallelepiped having the width W of 14 mm, the depth D of 12 mm and the height H of 18 mm.

Each of the blocks according to Examples 1 to 7 and Comparative Examples 5 and 6 was made by rapid heat treatment as follows.

In each example, the materials shown in Table 1 were mixed according to the proportions therein and molten at 1300° C. for 3 hours, to obtain molten glass (melting step). Next, the obtained molten glass was poured into a mold and cooled to room temperature, to form a glass blank (step of making a glass blank). Then, the glass blank was put into a furnace preheated to the heat-treating temperature shown in Table 1, to be kept at this heat-treating temperature for 30 minutes (rapid heat treatment). Thereafter the resultant was slowly cooled to room temperature (cooling step), to obtain the block.

In contrast, each of the blocks according to Comparative Examples 1 to 4 was made by conventional heat treatment as follows.

In each example, the materials shown in Table 1 were mixed according to the proportions therein and molten at 1300° C. for 3 hours, to obtain molten glass (melting step). Next, the obtained molten glass was poured into a mold and cooled to room temperature, to form a glass blank (step of making a glass blank). Then, the obtained glass blank was heated and kept at 650° C. for 60 minutes, and then heated to 850° C. to be kept for 10 minutes (conventional heat treatment). Thereafter the resultant was slowly cooled to room temperature (cooling step), to obtain the block.

Table 1 shows the content of each component in terms of mass %. As can be seen from Table 1, the components other than coloring materials are the same in Example 1 and Comparative Example 1, Example 2 and Comparative Example 2, Example 3 and Comparative Example 3, and Example 4 and Comparative Example 4 respectively.

Table 1 also shows the type of heat treatment, heat-treating temperature in the case of rapid heating, the type of the main crystalline phase of the obtained block ("LDS" represents lithium disilicate, and "LS" represents lithium metasilicate), the proportion (%) of crystals having a length of at least 0.5 μm, which was obtained by the above described method, and machinability. Blanks in rows of component in Table 1 show that the corresponding content was 0 mass %.

The main crystal was measured by means of an X-ray diffractometer (Empyrean™; manufactured by Spectris Co., Ltd.); as a result of a quantitative analysis by the Rietveld refinement, a crystalline phase the precipitation rate of crystals of which was the highest in the observed crystalline phases was defined as the main crystalline phase.

"Proportion" is the foregoing proportion of crystals having a length of at least 0.5 μm, and is the proportion (%) of the area obtained by the above described method.

For "machinability", two conventional blocks for processing were prepared as References 1 and 2. Each block was as follows:

(Reference 1) a block whose main crystalline phase was of lithium metasilicate, containing 72.3 mass % of $SiO_2$, 15.0 mass % of $Li_2O$, and 1.6 mass % of $Al_2O_3$; and (Reference 2) a block including almost the same proportion of a crystalline phase of lithium metasilicate and a crystalline phase of lithium disilicate, containing 56.3 mass % of $SiO_2$, 14.7 mass % of $Li_2O$, and 2.1 mass % of $Al_2O_3$.

For Examples and Comparative Examples, the degrees of the processing time, wear and tear on a tool, and chipping when the blocks were processed by a ceramic processing machine (CEREC™ MC XL; manufactured by Sirona Dental Systems, Inc.) compared to the blocks of References 1 and 2 were each evaluated. Blocks whose evaluation results of the processing time, wear and tear on a tool, and chipping were all better than those of the blocks of References 1 and 2 were represented as "good", and blocks whose evaluation results of any of the processing time, wear and tear on a tool, and chipping were worse than those of the blocks of References 1 and 2 were represented as "bad".

TABLE 1

| | | Example 1 | Example 2 | Example 3 | Example 4 | Example 5 | Example 6 | Example 7 | Comparative Example 1 |
|---|---|---|---|---|---|---|---|---|---|
| Component | $SiO_2$ | 71.0 | 71.5 | 72.7 | 70.7 | 65.5 | 71.0 | 71.0 | 71.0 |
| | $Li_2O$ | 12.8 | 13.7 | 11.7 | 11.9 | 14.4 | 12.8 | 12.8 | 12.8 |
| | $Al_2O_3$ | 5.2 | 5.3 | 5.3 | 5.2 | 5.0 | 5.2 | 5.2 | 5.2 |
| | $P_2O_5$ | 3.0 | 3.0 | 2.5 | 2.6 | 6.4 | 3.0 | 3.0 | 3.0 |
| | $K_2O$ | 1.4 | 1.4 | 2.5 | 2.4 | 2.0 | 1.4 | 1.4 | 1.4 |
| | $Na_2O$ | 2.1 | 2.1 | 1.2 | 1.1 | 1.3 | 2.1 | 2.1 | 2.1 |
| | $ZrO_2$ | 1.0 | 1.8 | 1.9 | 3.1 | 3.1 | 1.0 | 1.0 | 1.0 |
| | SrO | | | | 1.3 | | | | |
| | $TiO_2$ | | | | 0.3 | | | | |
| | $La_2O_3$ | | 0.5 | | | | | | |
| | BaO | | | 1.0 | | | | | |
| | $V_2O_5$ | 1.1 | 0.2 | 0.2 | 0.4 | 0.6 | 1.1 | 1.1 | 1.0 |
| | $CeO_2$ | 0.7 | 0.2 | 0.1 | 0.1 | 0.5 | 0.7 | 0.7 | 1.0 |
| | $Er_2O_3$ | 0.6 | 0.4 | 0.3 | 0.4 | 1.1 | 0.8 | 0.8 | 0.5 |
| | MnO | 0.1 | | | 0.1 | 0.1 | 0.2 | 0.2 | 0.4 |
| | $Fe_2O_3$ | 0.4 | | 0.1 | 0.2 | | 0.2 | 0.2 | 0.5 |
| | $Tb_4O_7$ | 0.7 | | 0.5 | 0.1 | | 0.6 | 0.6 | 0.2 |
| Heat treatment | | rapid heating 750° C. | rapid heating 850° C. | rapid heating 800° C. | rapid heating 820° C. | rapid heating 850° C. | rapid heating 830° C. | rapid heating 900° C. | conventional heating |
| Main crystalline phase | | LDS | LDS | LDS | LDS | LDS | LDS | LDS | LDS |
| Proportion | | at most 1% | at most 1% | at most 1% | at most 1% | at most 1% | at most 1% | at most 1% | 27% |
| Machinability | | good | good | good | good | good | good | good | bad |

| | | Comparative Example 2 | Comparative Example 3 | Comparative Example 4 | Comparative Example 5 | Comparative Example 6 |
|---|---|---|---|---|---|---|
| Component | $SiO_2$ | 71.5 | 72.7 | 70.7 | 71.5 | 71.5 |
| | $Li_2O$ | 13.7 | 11.7 | 11.9 | 13.7 | 13.7 |
| | $Al_2O_3$ | 5.3 | 5.3 | 5.2 | 5.3 | 5.3 |
| | $P_2O_5$ | 3.0 | 2.5 | 2.6 | 3.0 | 3.0 |
| | $K_2O$ | 1.4 | 2.5 | 2.4 | 1.4 | 1.4 |
| | $Na_2O$ | 2.1 | 1.2 | 1.1 | 2.1 | 2.1 |
| | $ZrO_2$ | 1.8 | 1.9 | 3.1 | 1.8 | 1.8 |
| | SrO | | | 1.3 | | |
| | $TiO_2$ | | | 0.3 | | |
| | $La_2O_3$ | 0.5 | | | 0.5 | 0.5 |

TABLE 1-continued

| | | | | | |
|---|---|---|---|---|---|
| BaO | | 1.0 | | | |
| $V_2O_5$ | 0.6 | 0.4 | 0.1 | 0.2 | 0.2 |
| $CeO_2$ | 0.1 | 0.1 | 0.4 | 0.2 | 0.2 |
| $Er_2O_3$ | 0.1 | 0.4 | 0.2 | 0.4 | 0.4 |
| MnO | | 0.1 | 0.1 | | |
| $Fe_2O_3$ | | 0.2 | | | |
| $Tb_4O_7$ | | | | | |
| Heat treatment | con-ventional heating | con-ventional heating | con-ventional heating | rapid heating 700° C. | rapid heating 950° C. |
| Main crystalline phase | LDS | LDS | LDS | LS | deformed by softening |
| Proportion | at most 50% | at most 50% | at most 50% | — | |
| Machinability | bad | bad | bad | | |

As can be seen from Table 1, machinability of the blocks for dental prostheses of Examples are good although the main crystalline phase thereof was of lithium disilicate. In Examples, "proportion" was suppressed lower than the proportions in Comparative Examples.

It is also found that different producing steps lead to largely different machinability and proportion although the components other than coloring materials are the same in Example 1 and Comparative Example 1, Example 2 and Comparative Example 2, Example 3 and Comparative Example 3, and Example 4 and Comparative Example 4. In Comparative Example 5, lithium disilicate could not be obtained as the main crystalline phase. In Comparative Example 6, softening occurred.

The blocks of any of Examples and Comparative Examples had necessary strength, and satisfied the above described preferred requirements concerning voids and particulate matters.

REFERENCE SIGNE LIST 10 block for dental prostheses
The invention claimed is:

1. A method of producing a block for dental prostheses before cutting to form a dental prosthesis, the method comprising:
   exposing a glass blank at a temperature lower than a temperature at which crystals of lithium metasilicate are generated, to an atmosphere at a temperature equal to or higher than a temperature at which crystals of lithium disilicate are generated and lower than a melting point of the crystals of lithium disilicate, to heat the glass blank so that a main crystalline phase of the glass blank is of lithium disilicate,
   wherein heating of the glass blank is performed so that, in a partially enlarged cross sectional view of the block in a field of view of 5 μm in a width direction and 5 μm in a depth direction, a proportion of a total area of crystals having a length of at least 0.5 μm and appearing within the field of view to an area of the field of view is at most 1%,
   wherein the block consists essentially of 60 mass % to 80 mass % of $SiO_2$, 10 mass % to 20 mass % of $Li_2O$, 5.2 mass % to 15 mass % of $Al_2O_3$, and
   at least one component selected from the group consisting of
   $Na_2O$: at most 2.8 mass %,
   $K_2O$: at most 10 mass %,
   CaO: at most 3 mass %,
   SrO: at most 10 mass %,
   BaO: at most 10 mass %,
   MgO: at most 3 mass %,
   $Rb_2O$: at most 2.8 mass %,
   $Cs_2O$: at most 2.8 mass %,
   $Fr_2O$: at most 2.8 mass %,
   BeO: at most 3 mass %,
   RaO: at most 10 mass %,
   respective oxides of Zr, P and Ti, and
   a coloring material.

2. The method according to claim 1, further comprising natural cooling after said exposing to heat the glass blank.

3. The method according to claim 1, wherein the temperature of the atmosphere is 750° C. to 900° C.

4. The method according to claim 1, wherein said exposing the glass blank to the atmosphere is putting the glass blank in a heating apparatus.

5. A method of producing a dental prosthesis, the method comprising:
   producing a block for dental prostheses by the producing method according to claim 1, to machine the block.

6. The method according to claim 5, wherein said machining is cutting.

7. The method according to claim 1, wherein the block does not contain $La_2O_3$.

* * * * *